United States Patent
Zhong et al.

(10) Patent No.: US 9,730,969 B2
(45) Date of Patent: Aug. 15, 2017

(54) NUTRITIONAL COMPOSITIONS FOR PROMOTING GUT BARRIER FUNCTION AND AMELIORATING VISCERAL PAIN

(71) Applicant: Mead Johnson Nutrition Company, Glenview, IL (US)

(72) Inventors: Yan Zhong, Shanghai (CN); Teartse Tim Lambers, Nijmegen (NL); Gabriele Gross, Nijmegen (NL); Sarmauli Manurung, Nijmegen (NL); Eric A. F. van Tol, Arnhem (NL); Rosaline Waworuntu, Evansville, IN (US)

(*) Notice: Subject to any disclaimer, the term of this patent is extended or adjusted under 35 U.S.C. 154(b) by 0 days.

(21) Appl. No.: 14/934,559

(22) Filed: Nov. 6, 2015

(65) Prior Publication Data

US 2017/0128500 A1    May 11, 2017

(51) Int. Cl.
    *A61K 35/747*    (2015.01)
    *A23L 1/29*      (2006.01)
    *A23L 1/30*      (2006.01)

(52) U.S. Cl.
    CPC .......... *A61K 35/747* (2013.01); *A23L 1/296* (2013.01); *A23L 1/3014* (2013.01); *A23V 2002/00* (2013.01)

(58) Field of Classification Search
    CPC .................................................. A61K 35/747
    See application file for complete search history.

(56) References Cited

U.S. PATENT DOCUMENTS 4,791,193 A    12/1988    Okonogi et al.
5,032,399 A    7/1991    Gorbach et al.
(Continued)

FOREIGN PATENT DOCUMENTS

AU    2006230772    11/2006
CN    1663573    9/2005
(Continued)

OTHER PUBLICATIONS

Rubaltelli et al., "Probiotics feeding prevents necrotizing enterocolitis in preterm infants: a prospective double-blind study," Pediatric Academic Societies and American Academy of Pediatrics Joint Meeting, meeting abstract No. 2042, 2000.*

(Continued)

*Primary Examiner* — Rosanne Kosson
(74) *Attorney, Agent, or Firm* — OspreyIP, pllc; James R. Cartiglia; Bethany J. Whelan

(57) ABSTRACT

The present disclosure is directed to methods for i) promoting gut regeneration, ii) promoting gut maturation and/or adaptation, iii) supporting gut barrier resistance and/or iv) protecting gut barrier function in a pediatric subject comprising administering to the pediatric subject a composition comprising an effective amount of a soluble mediator preparation derived from a late-exponential growth phase of a probiotic batch-cultivation process, such as *Lactobacillus rhamnosus* GG (LGG). The present methods advantageously provide the gut-protection benefits of LGG soluble mediators without introducing live bacterial culture to individuals with impaired gut barrier function. In some embodiments, the pediatric subject has impaired gut barrier function and/or short bowel syndrome. The present disclosure in other embodiments, directed methods for reducing visceral pain in a pediatric subject comprising administering to the pediatric subject a composition comprising an effective amount of a soluble mediator preparation from a late-exponential growth phase of a probiotic batch-cultivation process, such as LGG.

17 Claims, 5 Drawing Sheets

(56) References Cited

U.S. PATENT DOCUMENTS

| | | | |
|---|---|---|---|
| 5,374,567 A | 12/1994 | Cartagena | |
| 5,397,591 A | 3/1995 | Kyle | |
| 5,550,156 A | 8/1996 | Kyle | |
| 5,849,885 A | 12/1998 | Nuyens | |
| 5,861,491 A | 1/1999 | Nuijens | |
| 5,919,913 A | 7/1999 | Nuyens | |
| 6,620,326 B1 | 9/2003 | Lihme | |
| 6,682,744 B1* | 1/2004 | Panigrahi | A61K 31/00 424/184.1 |
| 6,977,046 B2 | 12/2005 | Hubbuch | |
| 7,368,141 B2 | 5/2008 | Lihme | |
| 7,812,138 B2 | 10/2010 | Lihme | |
| 8,476,058 B2 | 7/2013 | Simon et al. | |
| 2002/0081311 A1 | 6/2002 | Shanahan | |
| 2004/0214304 A1 | 10/2004 | Collins et al. | |
| 2006/0251635 A1 | 11/2006 | Glenn et al. | |
| 2007/0298080 A1 | 12/2007 | Desreumaux et al. | |
| 2011/0105385 A1 | 5/2011 | Fasano | |
| 2011/0217402 A1 | 9/2011 | van Tol et al. | |
| 2011/0274789 A1 | 11/2011 | Mkelsaar et al. | |
| 2013/0195822 A1 | 8/2013 | Legrain-Raspaud et al. | |
| 2013/0251829 A1 | 9/2013 | van Tol et al. | |
| 2015/0290260 A1 | 10/2015 | Chichlowski et al. | |
| 2015/0305384 A1 | 10/2015 | Chichlowski et al. | |

FOREIGN PATENT DOCUMENTS

| | | |
|---|---|---|
| CN | 104509864 | 4/2015 |
| FR | 2917623 | 12/2008 |
| JP | 2005068092 | 3/2005 |
| JP | 2008212006 | 9/2008 |
| JP | 2010083881 | 4/2010 |
| KR | 20110124516 | 12/2008 |
| WO | 9200799 | 1/1992 |
| WO | 9717132 | 5/1997 |
| WO | 0218237 | 3/2002 |
| WO | 2005034971 | 4/2005 |
| WO | 2005112976 | 12/2005 |
| WO | 2007132359 | 11/2007 |
| WO | 2013142403 | 9/2013 |
| WO | 2015156942 | 10/2015 |
| WO | 2015164021 | 10/2015 |

OTHER PUBLICATIONS

Agostini, S., et al., "A marketed fermented dairy product containing Bifidobacterium lactis CNCM I-2494 suppresses gut hypersensitivity and colonic barrier disruption induced by acute stress in rats," Neurogastroenterol Motil (2012) 24, 376-e172.

Ait-Belgnaoui, A., et al., "Probiotic gut effect prevents the chronic psychological stress-induced brain activity abnormality in mice," Neurogastroenterol Motil (2014) 26, 510-520.

Benton, D., et al., "Impact of consuming a milk drink containing a probiotic on mood and cognition," European Journal of Clinical Nutrition (2007) 61, 355-361.

Bermudez-Brito, M., et al., "Lactobacillus rhamnosus and its cell-free culture supernatant differentially modulate inflammatory biomarkers in *Escherichia coli*-challenged human dendritic cells," British Journal of Nutrition, Dec. 9, 2013 doi:10.1017/S0007114513004303.

Bravo, J., et al., "Ingestion of Lactobacillus strain regulates emotional behavior and central GABA receptor expression in a mouse via the vagus nerve," PNAS, vol. 108 No. 38, 16050-16055, Sep. 20, 2011.

Campeotto, F., et al., "A fermented formula in pre-term infants: clinical tolerance, gut microbiota, down-regulation of faecal calprotectin and up-regulation of faecal secretory IgA," British Journal of Nutrition (2011), 105, 1843-1851.

Carlsson, A., et al., "Faecalibacterium prausnitzii supernatant improves intestinal barrier function in mice DSS colitis," Scandinavian Journal of Gastroenterology. 2013; 48: 1136-1144.

Choi, C., et al., "Effect of Lactobacillus GG and conditioned media on IL-1b-induced IL-8 production in Caco-2 cells," Scandinavian Journal of Gastroenterology, 2008; 43: 938947.

Desbonnet, L., et al., "The probiotic Bifidobacteria infantis: An assessment of potential antidepressant properties in the rat," Journal of Psychiatric Research 43 (2009) 164-174.

Ditu, L., et al., "Immunomodulatory effect of non-viable components of probiotic culture stimulated with heat-inactivated *Escherichia coli* and Bacillus cereus on holoxenic mice," Microbial Ecology in Health & Disease 2014, 25: 23239—http://dx.doi.org/10.3402/mehd.v25.23239.

Duncker, S., et al., "The D-alanine content of lipoteichoic acid is crucial for Lactobacillus plantarum-mediated protection from visceral pain perception in a rat colorectal distension model," Neurogastroenterol Motil (2008) 20, 843-850.

Escamilla, J., et al., "Cell-Free Supernatants from Probiotic Lactobacillus casei and Lactobacillus rhamnosus GG Decrease Colon Cancer Cell Invasion In Vitro," Nutrition and Cancer, 64:6, 871-878, 2012 DOI: 10.1080/01635581.2012700758.

Eutamene, H., et al., "Synergy between Lactobacillus paracasei and Its Bacterial Products to Counteract Stress-Induced Gut Permeability and Sensitivity Increase in Rats1,2," J. Nutr. 137: 1901-1907, 2007.

Ewaschuk, J. et al., "Secreted bioactive factors from Bifidobacterium infantis enhance epithelial cell barrier function," Am J Physiol Gastrointest Liver Physiol 295: G1025-G1034, 2008.

Gareau, M., et al., "Probiotic treatment of rat pups normalises corticosterone release and ameliorates colonic dysfunction induced by maternal separation," Gut 2007;56:1522-1528.

Harb, H., et al., "Neonatal supplementation of processed supernatant from Lactobacillus rhamnosus GG improves allergic airway inflammation in mice later in life," Clinical & Experimental Allergy, 43, 353-364 2012.

Hsiao, E., et al., "The microbiota modulates gut physiology and behavioral abnormalities associated with autism," Cell. Dec. 19, 2013; 155(7): 1451-1463.

Kamiya, T., et al., "Inhibitory effects of Lactobacillus reuteri on visceral pain induced by colorectal distension in Sprague-Dawley rats," Gut 2006;55:191-196.

Kannampalli, P. et al., "Probiotic Lactobacillus rhamnosus GG (LGG) and prebiotic prevent neonatal inflammation-induced visceral hypersensitivity in adult rats," Neurogastroenterol Motil (2014).

Laval, L., et al., "Lactobacillus rhamnosus CNCM I-3690 and the commensal bacterium Faecalibacterium prausnitzii A2-165 exhibit similar protective effects to induced barrier hyper-permeability in mice," Gut Microbes, 6:1, 1-9, 2015, DOI: 104161/19490976.2014. 990784.

Lin, P., et al., "The Probiotic Lactobacillus GG may Augment Intestinal Host Defense by Regulating Apoptosis and Promoting Cytoprotective Responses in the Developing Murine Gut," Pediatric Research, vol. 64, No. 5, 2008.

Ling, J., et al "Perspectives on Interactions Between Lactoferrin and Bacteria," Biochemistry and Cell Biology, pp. 275-281 (2006).

McKernan, D., et al., "The probiotic Bifidobacterium infantis 35624 displays visceral antinociceptive effects in the rat," Neurogastroenterol Motil (2010) 22, 1029-e268.

Messoaoudi, M., et al., "Beneficial psychological effects of a probiotic formulation (Lactobacillus helveticus R0052 and Bifidobacterium longum R0175) in healthy human volunteers," Gut Microbes, 2:4, 256-261.

Orlando, A., et al., "Lactobacillus GG restoration of the gliadin induced epithelial barrier disruption: the role of cellular polyamines," BMC Microbiology 2014, 14:19.

Patel, R., et al., "Probiotic Bacteria Induce Maturation of Intestinal Claudin 3 Expression and Barrier Function," The American Journal of Pathology, vol. 180, No. 2, Feb. 2012.

Reddy, V., et al., "Role of Probiotics in Short Bowel Syndrome in Infants and Children—A Systematic Review," Nutrients 2013, 5, 679-699; doi:10.3390/nu5030679.

Rousseaux, C., et al., "Lactobacillus acidophilus modulates intestinal pain and induces opioid and cannabinoid receptors," Nature Medicine, 13(1): 35-37, Jan. 2007.

(56) References Cited

OTHER PUBLICATIONS

Savignac, H., et al., "Bifidobacteria modulate cognitive processes in an anxious mouse," Behavioural Brain Research 287 (2015) 59-72.
Segawa, S., et al., "Probiotic-Derived Polyphosphate Enhances the Epithelial Barrier Function and Maintains Intestinal Homeostasis through Integrin-p38 MAPK Pathway," PLoS One 6(8) 2011: e23278. doi:10.1371/journal.pone.0023278.
Sentongo, T., et al., "Intestinal Permeability and Effects of Lactobacillus rhamnosus Therapy in Children With Short Bowel Syndrome," Journal of Pediatric Gastroenterology and Nutrition, 46:41-47, 2008.
Seth, A., et al. "Probiotics ameliorate the hydrogen peroxide-induced epithelial barrier disruption by a PKC- and MAP kinase-dependent mechanism," Am J Physiol Gastrointest Liver Physiol 294: G1060-G1069, 2008.
Shiou, S., et al. "Synergistic Protection of Combined Probiotic Conditioned Media against Neonatal Necrotizing Entercolitis-Like Intestinal Injury," PLoS One 8(5) 2013: e65108. Doi:10.1371/journal.pone.0065108.
Tillisch, K., et al., "Consumption of Fermented Milk Product With Probiotic Modulates Brain Activity," Gastroenterology 2013;144:1394-1401.
Tsilingiri, K. et al., "Probiotic and postbiotic activity in health and disease: comparison on a novel polarized ex-vivo organ culture model," Gut 2012;61:1007e1015. doi:10.1136/gutjnl-2011-300971.
Wang, L., et al., "Activation of Epidermal Growth Factor Receptor Mediates Mucin Production Stimulated by p40, a Lactobacillus rhamnosus GG-derived Protein," The Journal of Biological Chemistry vol. 289, No. 29, pp. 20234-20244, Jul. 18, 2014.
Wang, Y., et al., "Lactobacillus rhamnosus GG culture supernatant ameliorates acute alcohol-induced intestinal permeability and liver injury," Am J Physiol Gastrointest Liver Physiol 303: G32-G41, 2012.
Yadomae, T., "Structure and biological activities of fungal beta-1,3-glucans."Yakugaku Zasshi. 2000;120:413-431, English abstract only; Examiner cannot read Japanese.

Yan, F., et al., "Colon-specific delivery of a probiotic-derived soluble protein ameliorates intestinal inflammation in mice through an EGFR-dependent mechanism," The Journal of Clinical Investigation, vol. 121 No. 6, Jun. 2011, pp. 2242-2253.
Yan, F., et al., "Soluble Proteins Produced by Probiotic Bacteria Regulate Intestinal Epithelial Cell Survival and Growth," Gastroenterology. Feb. 2007; 132(2): 562-575. doi:10.1053/j.gastro.2006.11.022.
Yoda, K, et al., "Lactobacillus GG-fermented milk prevents DSS-induced colitis and regulates intestinal epithelial homeostasis through activation of epidermal growth factor receptor," Eur J Nutr. Feb. 2014 ; 53(1): 105-115. doi:10.1007/s00394-013-0506-x.
Zhao, H., et al., "Inhibition of miR122a by Lactobacillus rhamnosus GG culture supernatant increases intestinal occludin expression and protects mice from alcoholic liver disease," Toxicology Letters 234 (2015) 194-200.
Agyekum, A.K., et al., "Probiotics Reduce Pathogen Invasion in Fetal and Neonatal Tissues," 51st Annual Meeting of the Teratology Society, vol. 91, May 5, 2011, p. 373, XP055037868.
Collado, M.C., et al., "Specific probiotic strains and their combinations counteract adhesion of Enterobacter sakazakii to intestinal mucus," Fems Microbiology Letters, vol. 285, No. 1, Aug. 1, 2008, pp. 58-64 XP055037880.
Collado, M.C., et al., "In vitro analysis of probiotic strain combinations to inhibit pathogen adhesion to human intestinal mucus," Food Research International, Elsevier, Amsterdam, NL, vol. 40, No. 5, Apr. 17, 2007, pp. 629-636, XP022032079.
Collado, M.C., et al., "Role of commercial probiotic strains against human pathogen adhesion to intestinal mucus," Letters in Applied Microbiology, vol. 45, No. 4, Oct. 1, 2007, pp. 454-460, XP055037881.
Collado, M.C., et al., "Development of New Probiotic by Strain Combinations: Is It Possible to Improve the Adhesion to Intestinal Mucus?," Journal of Dairy Science, American Dairy Science Association, U.S., vol. 90, No. 6, Jun. 1, 2007, pp. 2710-2716, XP026955939.

\* cited by examiner

FIG. 1A-F Intestinal Morphology

*Fig. 2A-D*. Tight junction proteins level in small intestine
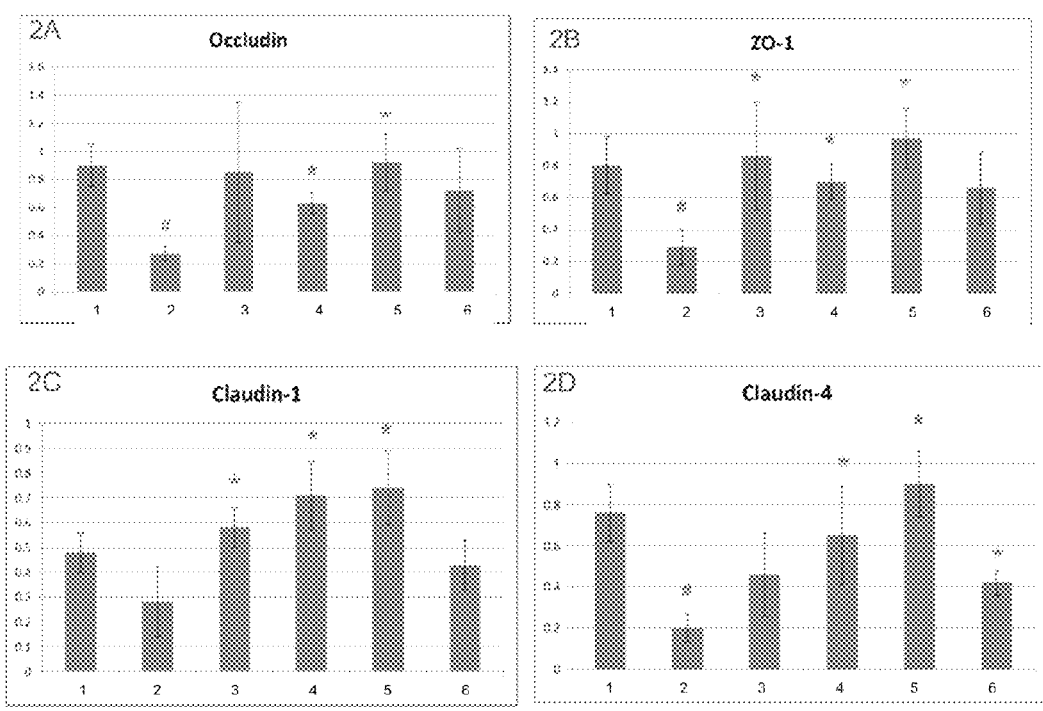
1: Sham
2: SBS
3: SBS + soluble mediator prep A
4: SBS + soluble mediator prep B
5: SBS + BCM
6: SBS + LGG

*Fig. 3A-D* Intestinal barrier function
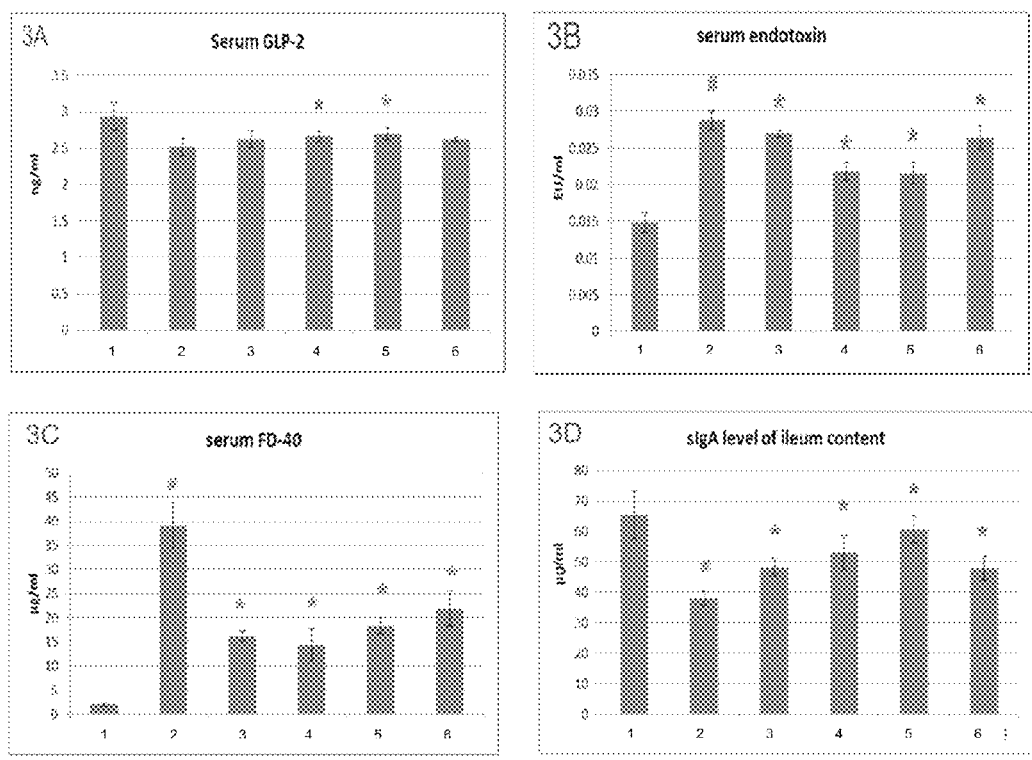
1: Sham
2: SBS
3: SBS + soluble mediator prep A
4: SBS + soluble mediator prep B
5: SBS + BCM
6: SBS + LGG

NUTRITIONAL COMPOSITIONS FOR PROMOTING GUT BARRIER FUNCTION AND AMELIORATING VISCERAL PAIN

TECHNICAL FIELD

The present disclosure relates generally to compositions and methods for promoting gut regeneration, promoting gut maturation, supporting gut barrier resistance and/or protecting gut barrier function in infants and young children with impaired and/or immature gut barrier function and/or short bowel syndrome. The present disclosure also relates to compositions and methods for reducing visceral pain disorders and perception. More particularly, the present disclosure relates to compositions comprising a culture supernatant from a late-exponential growth phase of a probiotic batch cultivation process, and methods of administering them.

BACKGROUND

Gut Barrier Function

The intestinal barrier provides protection from potentially harmful agents in the intestinal lumen, while allowing absorption of nutrients. Several mechanisms are involved in gut barrier function, such as intestinal morphological structure, systemic and local inflammation, intestinal bacterial translocation, and gut resistance. Gut barrier integrity may be compromised or disrupted during processes of intestinal inflammation, infection, allergic sensitization as well as a number of autoimmune diseases. More specifically, these mechanisms are potentially impaired in preterm and/or low birth weight infants, suffering from infections, congenital intestinal malformations, necrotizing enterocolitis (NEC) and short bowel syndrome (SBS).

Infections, such as rotavirus, and villous atrophy caused by, for example celiac disease, can lead to altered intestinal barrier properties. Impaired gut barrier function may result in reduction of villous height and increased crypt depth. SBS is defined as the malabsorptive state when the functioning gut mass is reduced below the amount necessary for adequate digestion and absorption of food and fluid that eventually leads to clinical nutrient deficiencies and requires parenteral nutrition (PN) support. Some children are born with a congenital short bowel, while others acquire it surgically, for example for surgical treatment of necrotizing enterocolitis. SBS is a leading cause of intestinal failure in neonates, infants and young children, with high prevalence in premature infants. Intestinal bacterial overgrowth and bacterial translocation is a major complication of SBS, and is caused by disrupted gut barrier function.

As suggested by animal and clinical studies, intestinal bacterial overgrowth and translocation in infants with impaired gut barrier function may not only be a factor involved in gut-derived infection, but also may further impair the rehabilitation process. It also may impair gut regeneration, maturation, differentiation, and epithelial functioning. The aforementioned impairments can result in malabsorption. Intestinal gut flora also contribute to a healthy and intact gut barrier due to their metabolic, trophic, and immune modulatory properties.

Probiotics may be helpful in pediatric patients with impaired gut barrier function due to any of the aforementioned causes. Nevertheless, the administration of viable bacteria to pediatric subjects, and particularly preterm infants, with impaired intestinal defenses and immature gut barrier function may not be feasible due to the risk of bacteremia. Moreover, soluble factors secreted from viable probiotic material may be involved in some of the beneficial effects of probiotic bacteria. Therefore, there is a need for compositions that can provide the benefits of probiotics without introducing viable bacteria into the intestinal tract of pediatric subjects suffering from impaired/immature gut barrier function, such as SBS or NEC.

Visceral Pain Disorders in Pediatric Subjects

The early postnatal period is normally a stress-hyporesponsive period during which time there is an intense phase of neuronal growth and myelination. Stressful episodes such as food intolerance, allergic or non-allergic inflammation, colic, inflammatory bowel syndrome, and infections during this critical window can have long lasting effects starting in early life. Such effects include visceral hypersensitivity and reduced diversity of intestinal microbiota. Probiotics may be useful in reducing visceral hypersensitivity, but information on the effects of probiotic soluble mediators is lacking. Therefore, there is a need for compositions and methods for reducing visceral pain in infants and children, and in particular, pediatric groups with increased visceral sensitivity.

BRIEF SUMMARY

Briefly, the present disclosure is directed to methods for i) promoting gut regeneration, ii) promoting gut maturation and/or adaptation, iv) supporting gut barrier resistance and/or v) protecting gut barrier function in a pediatric subject comprising administering to the pediatric subject a composition comprising an effective amount of a soluble mediator preparation from a late-exponential growth phase of a probiotic batch-cultivation process. In certain embodiments, the probiotic is *Lactobacillus rhamnosus* GG (LGG). The present methods advantageously provide similar gut-protection benefits as viable probiotics, such as LGG, without introducing live bacterial culture to individuals with impaired gut barrier function. In some embodiments, the pediatric subject has impaired gut barrier function and/or short bowel syndrome and/or NEC. In more particular embodiments, the pediatric subject is an infant or a premature infant.

The present disclosure also provides compositions comprising a soluble mediator preparation from a late-exponential growth phase of a probiotic batch-cultivation process. In certain embodiments, the composition is an infant formula for i) promoting gut regeneration, ii) promoting gut maturation and/or adaptation, iii) promoting gut barrier adaptation, iv) supporting gut barrier resistance and/or v) protecting gut barrier function in an infant comprising: up to about 7 g/100 Kcal of a fat or lipid; up to about 5 g/100 Kcal of a protein source; up to about 22 g/100 kcal of a carbohydrate source; and a soluble mediator preparation from a late-exponential growth phase of a probiotic batch-cultivation process. In more particular embodiments, the probiotic is LGG.

The present disclosure in other embodiments, is related to methods for reducing visceral pain in a pediatric subject comprising administering to the pediatric subject a composition comprising an effective amount of a soluble mediator preparation from a late-exponential growth phase of a probiotic batch-cultivation process. In certain embodiments, the probiotic is *Lactobacillus rhamnosus* GG (LGG). In some embodiments, the pediatric subject has increased visceral sensitivity due to visceral pain disorders, gastrointestinal pain or discomfort or colic resulting from inflammatory bowel syndrome (IBS), dietary intolerance or allergy (such as cow's milk allergy).

In still other embodiments, the present disclosure provides compositions comprising a soluble mediator preparation from a late-exponential growth phase of a probiotic batch-cultivation process for reducing visceral pain in a pediatric subject comprising: up to about 7 g/100 Kcal of a fat or lipid; up to about 5 g/100 Kcal of a protein source; up to about 22 g/100 kcal of a carbohydrate source; and a soluble mediator preparation from a late-exponential growth phase of a probiotic batch-cultivation process. In more particular embodiments, the probiotic is LGG.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

FIGS. 2A-D are graphs of the mean expression of tight junction proteins among the six treatment groups (2A: occludin; 2B: ZO-1; 2C: claudin-1; 2D: claudin-4). Six treatment groups were 1: Sham; 2: SBS; 3: SBS+soluble mediator preparation A; 4: SBS+soluble mediator preparation B; 5: SBS+BCM; 6: SBS+LGG.

FIGS. 3A-D are graphs depicting measurement of intestinal barrier permeability and resistance among all six experimental groups (2A: serum FD-40 levels; 2B: serum endotoxin levels; 2C: serum GLP-2 and 2D: sIgA levels of ileum content). Six experimental groups include 1: Sham; 2: SBS; group 3: SBS+soluble mediator preparation A; 4: SBS+soluble mediator preparation B; 5: SBS+BCM; 6: SBS+LGG. Values are means±sd. Means with different superscripts are statistically significant (P<0.05).

DETAILED DESCRIPTION

Figure 1A:
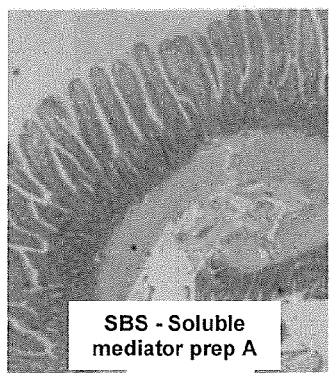
FIGS. 1A-F are images of ileum samples for each of six experimental groups demonstrating effects on intestinal morphology in rats using an SBS model (treatments with LGG soluble mediator preparation A, soluble mediator preparation B, bacteria culture medium, viable LGG, control SBS, and sham). The images demonstrate differences in villus height and crypt depth among these six treatment groups.
Figure 1B:
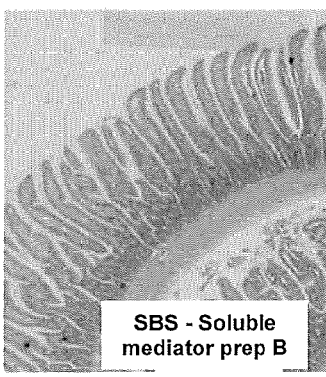
Figure 1C:
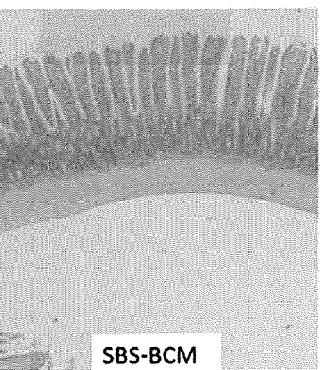
Figure 1D:
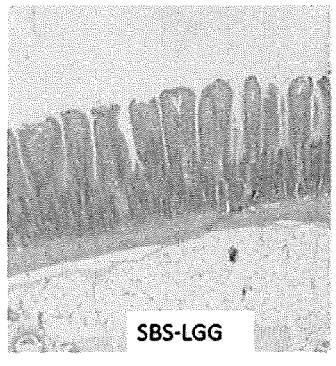
Figure 1E:
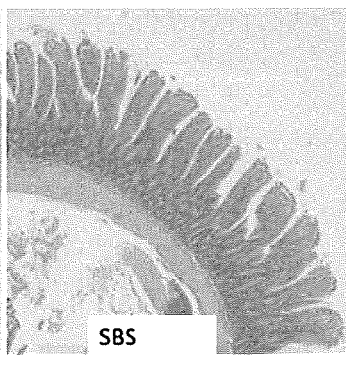
Figure 1F:
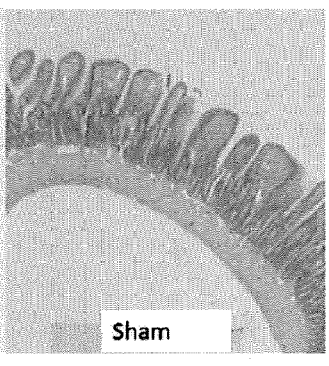

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to methods for i) promoting gut regeneration, ii) promoting gut maturation and/or adaptation, iii) supporting gut resistance and/or iv) protecting gut barrier function in a pediatric subject, comprising administering a composition comprising a culture supernatant from a late-exponential growth phase of a probiotic batch-cultivation process. The present disclosure further relates to compositions comprising a culture supernatant, and more particularly, a soluble mediator preparation, from a late-exponential growth phase of a probiotic, such as LGG, batch-cultivation process for use in i) promoting gut regeneration, ii) promoting gut maturation and/or adaptation, iii) supporting gut barrier resistance and/or iv) protecting gut barrier function in a pediatric subject.

In other embodiments, the present disclosure provides methods for reducing visceral pain in a pediatric subject comprising administering to the pediatric subject a composition comprising an effective amount of a culture supernatant from a late-exponential growth phase of a probiotic batch-cultivation process. In certain embodiments, the probiotic is LGG. In some embodiments, the pediatric subject has increased visceral sensitivity, suffers from recurrent gastrointestinal pain, colic, inflammatory bowel syndrome (IBS), dietary intolerance or allergy (such as cow's milk allergy).

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human no greater than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the 37th week of gestation. "Late preterm" means an infant form between the 34th week and the 36th week of gestation. "Full term" means an infant born after the end of the 37th week of gestation. "Low birth weight infant" means an infant born weighing less than 2500 grams (approximately 5 lbs, 8 ounces). "Very low birth weight infant" means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

The term "degree of hydrolysis" refers to the extent to which peptide bonds are broken by a hydrolysis method.

The term "partially hydrolyzed" means having a degree of hydrolysis which is greater than 0% but less than about 50%.

The term "extensively hydrolyzed" means having a degree of hydrolysis which is greater than or equal to about 50%.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Prebiotic" means a non-digestible food ingredient that beneficially affects the host by selectively stimulating the growth and/or activity of one or a limited number of bacteria in the digestive tract that can improve the health of the host.

As used herein, "lactoferrin from a non-human source" means lactoferrin which is produced by or obtained from a source other than human breast milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism. Exemplary non-human sourced lactoferrin includes bovine lactoferrin.

As used herein, "non-human lactoferrin" means lactoferrin that has an amino acid sequence that is different than the amino acid sequence of human lactoferrin.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional compositions of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

"Probiotic" means a microorganism with low or no pathogenicity that exerts a beneficial effect on the health of the host. The term "inactivated probiotic" means a probiotic wherein the metabolic activity or reproductive ability of the referenced probiotic has been reduced or destroyed. The "inactivated probiotic" does, however, still retain, at the cellular level, its cell structure or other structure associated with the cell, for example exopolysaccharide and at least a portion of its biological glycol-protein and DNA/RNA structure. As used herein, the term "inactivated" is synonymous with "non-viable".

Any probiotic known in the art may be used. In a particular embodiment, the probiotic may be selected from any *Lactobacillus* species, *Lactobacillus rhamnosus* GG (LGG) (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

In particular embodiments, the probiotic is *Lactobacillus rhamnosus* GG (*Lactobacillus* G.G., strain ATCC 53103). LGG is a bacterium that has been isolated from a fecal sample of a healthy human subject. It is widely recognized as a probiotic. It was disclosed in U.S. Pat. No. 5,032,399 to Gorbach, et al., which is herein incorporated in its entirety, by reference thereto. LGG is not resistant to most antibiotics, stable in the presence of acid and bile, and attaches avidly to mucosal cells of the human intestinal tract. It persists for 1-3 days in most individuals and up to 7 days in 30% of subjects. In addition to its colonization ability, LGG also beneficially affects mucosal immune responses. LGG is deposited with the depository authority American Type Culture Collection under accession number ATCC 53103.

While not wishing to be bound by theory, it is believed that a culture supernatant from batch cultivation of a probiotic, and in particular embodiments, LGG, promotes gut barrier function, particularly in subjects with impaired gut barrier function. It is further believed that the beneficial effects on gut barrier function can be attributed to the mixture of components (including proteinaceous materials, and possibly including (exo)polysaccharide materials) that are released into the culture medium at a late stage of the exponential (or "log") phase of batch cultivation of LGG. The composition will be hereinafter referred to as "soluble mediator preparation."

In other embodiments, it is believed that the present soluble mediator preparation is likely to result in measurable decrease of visceral hypersensitivity and abdominal discomfort in a pediatric population due to visceral pain disorders (recurrent abdominal pain, IBS, or colic) or due to diet intolerance and cow's milk allergy. In further embodiments, it is believed that the present soluble mediator preparation is likely to result in an increase in learning ability and improved memory.

A soluble mediator preparation of the present disclosure can be prepared as described below. Furthermore, preparation of an LGG soluble mediator preparation is described in US 20130251829 and US 20110217402, each of which is incorporated by reference in its entirety. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

The present disclosure further relates to processes for preparing a probiotic soluble mediator preparation. In a preferred embodiment, a composition according to the disclosure and/or embodiments thereof is obtainable by a process comprising the steps of (a) subjecting a probiotic such as LGG to cultivation in a suitable culture medium using a batch process; (b) harvesting a culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removal of any remaining cells using 0.22 μm sterile filtration to provide the soluble mediator preparation; (e) removing liquid contents from the soluble mediator preparation so as to obtain the composition.

In certain embodiments, secreted materials are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In a preferred embodiment of the present disclosure and embodiments thereof, harvesting of the culture supernatant is at a point in time of 75% to 85% of the duration of the exponential phase, and most preferably is at about ⅚ of the time elapsed in the exponential phase.

The term "cultivation" or "culturing" refers to the propagation of micro-organisms, in this case LGG, on or in a suitable medium. Such a culture medium can be of a variety of kinds, and is particularly a liquid broth, as customary in the art. A preferred broth, e.g., is MRS broth as generally used for the cultivation of lactobacilli. MRS broth generally comprises polysorbate, acetate, magnesium and manganese, which are known to act as special growth factors for lactobacilli, as well as a rich nutrient base. A typical composition comprises (amounts in g/liter): peptone from casein 10.0; meat extract 8.0; yeast extract 4.0; D(+)-glucose 20.0; dipotassium hydrogen phosphate 2.0; Tween® 80 1.0; tri-ammonium citrate 2.0; sodium acetate 5.0; magnesium sulphate 0.2; manganese sulphate 0.04.

In certain embodiments, the culture supernatant is incorporated into an infant formula or other nutritional composition. The harvesting of secreted bacterial products brings about a problem that the culture media cannot easily be deprived of undesired components. This specifically relates to nutritional products for relatively vulnerable subjects, such as infant formula or clinical nutrition. This problem is not incurred if specific components from a culture supernatant are first isolated, purified, and then applied in a nutritional product. However, it is desired to make use of a more complete culture supernatant. This would serve to provide a composition better reflecting the natural action of the probiotic (e.g. LGG).

Accordingly, it is desired to ensure that the composition harvested from LGG cultivation does not contain components (as may present in the culture medium) that are not desired, or generally accepted, in such formula. With reference to polysorbate regularly present in MRS broth, media for the culturing of bacteria may include an emulsifying non-ionic surfactant, e.g. on the basis of polyethoxylated sorbitan and oleic acid (typically available as Tween® polysorbates, such as Tween® 80). Whilst these surfactants are frequently found in food products, e.g. ice cream, and are generally recognized as safe, they are not in all jurisdictions considered desirable, or even acceptable for use in nutritional products for relatively vulnerable subjects, such as infant formula or clinical nutrition.

Therefore, in some embodiments, a preferred culture medium of the disclosure is devoid of polysorbates such as Tween 80. In a preferred embodiment of the disclosure and/or embodiments thereof the culture medium may comprise an oily ingredient selected from the group consisting of oleic acid, linseed oil, olive oil, rape seed oil, sunflower oil and mixtures thereof. It will be understood that the full benefit of the oily ingredient is attained if the presence of a polysorbate surfactant is essentially or entirely avoided.

More particularly, in certain embodiments, an MRS medium is devoid of polysorbates. Also preferably medium comprises, in addition to one or more of the foregoing oils, peptone (typically 0-10 g/L, especially 0.1-10 g/L), meat extract (typically 0-8 g/L, especially 0.1-8 g/L), yeast extract (typically 4-50 g/L), D(+) glucose (typically 20-70 g/L), dipotassium hydrogen phosphate (typically 2-4 g/L), sodium acetate trihydrate (typically 4-5 g/L), triammonium citrate (typically 2-4 g/L), magnesium sulfphate heptahydrate (typically 0.2-0.4 g/L) and/or manganous sulphate tetrahydrate (typically 0.05-0.08 g/L).

The culturing is generally performed at a temperature of 20° C. to 45° C., more particularly at 35° C. to 40° C., and more particularly at 37° C. In some embodiments, the culture has a neutral pH, such as a pH of between pH 5 and pH 7, preferably pH 6.

In some embodiments, the time point during cultivation for harvesting the culture supernatant, i.e., in the aforementioned late exponential phase, can be determined, e.g. based on the OD600 nm and glucose concentration. OD600 refers to the optical density at 600 nm, which is a known density measurement that directly correlates with the bacterial concentration in the culture medium.

The culture supernatant can be harvested by any known technique for the separation of culture supernatant from a bacterial culture. Such techniques are known in the art and include, e.g., centrifugation, filtration, sedimentation, and the like. In some embodiments, LGG cells are removed from the culture supernatant using 0.22 m sterile filtration. The probiotic soluble mediator preparation thus obtained may be used immediately, or be stored for future use. In the latter case, the preparation will generally be refrigerated, frozen or lyophilized. The preparation may be concentrated or diluted, as desired.

The soluble mediator preparation is believed to contain a mixture of amino acids, oligo- and polypeptides, and proteins, of various molecular weights. The composition is further believed to contain polysaccharide structures and/or nucleotides.

In some embodiments, the soluble mediator preparation of the present disclosure excludes lower molecular weight components, generally below 6 kDa, or even below 5 kDa. In these and other embodiments, the soluble mediator preparation does not include lactic acid and/or lactate salts. These lower molecular weight components can be removed, for example, by filtration or column chromatography. In some embodiments, the culture supernatant is subjected to ultrafiltration with a 5 kDa membrane in order to retain constituents over 5 kDa. In other embodiments, the culture supernatant is desalted using column chromatography to retain constituents over 6 kDa.

The soluble mediator preparation of the present disclosure can be formulated in various ways for administration to pediatric subjects. For example, the soluble mediator preparation can be used as such, e.g. incorporated into capsules for oral administration, or in a liquid nutritional composition such as a drink, or it can be processed before further use. Such processing generally involves separating the compounds from the generally liquid continuous phase of the supernatant. This preferably is done by a drying method, such as spray-drying or freeze-drying (lyophilization). In a preferred embodiment of the spray-drying method, a carrier material will be added before spray-drying, e.g., maltodextrin DE29.

Probiotic bacteria soluble mediator preparations, such as the LGG soluble mediator preparation of the present disclosure, advantageously possess gut barrier enhancing activity by promoting gut barrier regeneration, gut barrier maturation and/or adaptation, gut barrier resistance and/or gut barrier function. The present LGG soluble mediator preparation may accordingly be particularly useful in treating subjects, particularly pediatric subjects, with impaired gut barrier function, such as short bowel syndrome or NEC. The soluble mediator preparation may be particularly useful for infants and premature infants having impaired gut barrier function and/or short bowel syndrome.

Probiotic bacteria soluble mediator preparation, such as the LGG soluble mediator preparation of the present disclosure, also advantageously reduce visceral pain sensitivity in subjects, particularly pediatric subjects experiencing gastrointestinal pain, food intolerance, allergic or non-allergic inflammation, colic, IBS, and infections.

In order for the soluble mediator preparation of the disclosure to exert its beneficial effect on the gut barrier or visceral pain sensitivity, it is to be digested by a subject in need thereof. The form of administration of the soluble mediator preparation is not critical. In some embodiments, the composition is administered to a subject via tablets, pills, encapsulations, caplets, gel caps, capsules, oil drops, or sachets. In another embodiment, the composition is encapsulated in a sugar, fat, or polysaccharide.

In other embodiments, the soluble mediator preparation is incorporated into a nutritional composition, such as a children's nutritional product such as a follow-on formula, growing up milk, beverage, milk, yogurt, fruit juice, fruit-based drink, chewable tablet, cookie, cracker, or a milk powder. In other embodiments, the product may be an infant's nutritional product, such as an infant formula or a human milk fortifier. When the soluble mediator preparation is incorporated into a nutritional composition, it is in some embodiments, spray dried or freeze dried prior to incorporation.

The LGG soluble mediator preparation of the present disclosure, whether added in a separate dosage form or via a nutritional product, will generally be administered in an amount effective in promoting gut regeneration, promoting gut maturation and/or adaptation, improving gut barrier resistance and/or protecting gut barrier function. The effective amount is preferably equivalent to $1 \times 10^4$ to about $1 \times 10^{12}$ cell equivalents of live probiotic bacteria per kg body weight per day, and more preferably $10^8$-$10^9$ cell equivalents per kg body weight per day. In other embodiments, the amount of cell equivalents may vary from about $1 \times 10^4$ to about $1.5 \times 10^{10}$ cell equivalents of probiotic(s) per 100 Kcal. In some embodiments the amount of probiotic cell equivalents may be from about $1 \times 10^6$ to about $1 \times 10^9$ cell equivalents of probiotic(s) per 100 Kcal nutritional composition. In certain other embodiments the amount of probiotic cell equivalents may vary from about $1 \times 0'$ to about $1 \times 10^8$ cell equivalents of probiotic(s) per 100 Kcal of nutritional composition. Cell equivalent is based on the number of LGG cells at the endpoint of the LGG cultivation time before separating the supernatant for further processing.

In an embodiment, a soluble mediator preparation is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) cells removal using 0.22 μm sterile filtration; (e) removing liquid contents from the soluble mediator preparation so as to obtain the composition.

The present LGG soluble mediator preparation may also be administered with lactoferrin. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) (SEQ. ID No. 1) and 28 to 31 (RKVR) (SEQ. ID No. 2) are arginine-rich cationic domains in the N-terminus especially critical to the antimicrobial activities of lactoferrin. A similar region in the N-terminus is found in bovine lactoferrin (residues 17 to 42; FKCRRWQWRMK-KLGAPSITCVRRAFA) (SEQ. ID No. 3).

As described in "*Perspectives on Interactions Between Lactoferrin and Bacteria*" (BIOCHEMISTRY AND CELL BIOLOGY, pp 275-281 (2006)), lactoferrins from different host species may vary in their amino acid sequences though commonly possess a relatively high isoelectric point with positively charged amino acids at the end terminal region of the internal lobe. Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 55% homology with human lactoferrin and in some embodiments, at least 65% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin. In particular embodiments, the lactoferrin is bLF.

In one embodiment, lactoferrin is present in the nutritional composition in an amount ranging from about 10 mg/100 Kcal to about 200 mg/100 Kcal. In certain embodiments, the lactoferrin is present in an amount ranging from about 15 mg/100 Kcal to about 100 mg/150 Kcal. In still another embodiment, particularly where the nutritional composition is an infant formula, the lactoferrin is present in the nutritional composition in an amount ranging from about 60 mg/100 Kcal to about 150 mg/100 Kcal or about 60 mg/100 Kcal to about 100 mg/100 Kcal.

The bLF that is used in certain embodiments may be any bLF isolated from whole milk and/or having a low somatic cell count, wherein "low somatic cell count" refers to a somatic cell count less than 200,000 cells/mL. By way of example, suitable bLF is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The nutritional composition of the disclosure also contains DHA. DHA is present, in some embodiments, in an amount ranging from about 5 mg/100 Kcal to about 75 mg/100 Kcal, more preferably about 10 mg/100 Kcal to about 50 mg/100 Kcal. The DHA may be provided from any source of LCPUFAs. Other suitable LCPUFAs that may be present in certain embodiments of the present compositions include, but are not limited to, α-linoleic acid, γ-linoleic acid, linoleic acid, linolenic acid, eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

The source of DHA and ARA, when present, may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

The nutritional composition may also contain one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactose, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.1 g/100 Kcal to about 1 g/100 Kcal. In certain embodiments, the total amount of prebiotics present in the nutritional composition may be from about 0.3 g/100 Kcal to about 0.7 g/100 Kcal. Moreover, the nutritional composition may comprise a prebiotic component comprising PDX. In some embodiments, the prebiotic component comprises at least 20% w/w PDX, GOS or a mixture thereof.

The amount of PDX in the nutritional composition may, in an embodiment, be within the range of from about 0.1 g/100 Kcal to about 1 g/100 Kcal. In another embodiment, the amount of polydextrose is within the range of from about 0.2 g/100 Kcal to about 0.6 g/100 Kcal. In still other embodiments, the amount of PDX in the nutritional composition may be from about 0.1 g/100 kcal to about 0.5 g/100 kcal.

The prebiotic component also comprises GOS in some embodiments. The amount of GOS in the nutritional composition may, in an embodiment, be from about 0.1 g/100 Kcal to about 1.0 g/100 Kcal. In another embodiment, the amount of GOS in the nutritional composition may be from about 0.2 g/100 Kcal to about 0.5 g/100 Kcal. In yet another embodiment, the amount GOS in the nutritional composition may be from about 0.1 g/100 kcal to about 0.5 g/100 kcal.

It is further believed that PDX and GOS have beneficial effect on brain development via the gut-brain-immune axis and therefore, when present, act synergistically to enhance brain development, and particularly, neuronal maturation.

The nutritional compositions of the disclosure may comprise at least one protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins may be partially hydrolyzed or extensively hydrolyzed. In still other embodiments, the protein source comprises amino acids. In yet another embodiment, the protein source may be supplemented with glutamine-containing peptides.

In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Some people exhibit allergies or sensitivities to intact proteins, i.e. whole proteins, such as those in intact cow's milk protein or intact soy protein isolate-based formulas. Many of these people with protein allergies or sensitivities are able to tolerate hydrolyzed protein. Hydrolysate formulas (also referred to as semi-elemental formulas) contain protein that has been hydrolyzed or broken down into short peptide fragments and amino acids and as a result is more easily digested. In people with protein sensitivities or allergies, immune system associated allergies or sensitivities often result in cutaneous, respiratory or gastrointestinal symptoms such as vomiting and diarrhea. People who exhibit reactions to intact protein formulas often will not react to hydrolyzed protein formulas because their immune system does not recognize the hydrolyzed protein as the intact protein that causes their symptoms.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 20% to about 80%, or from about 30% to about 80%, or even from about 40% to about 60%. The degree of hydrolysis is the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Kjeldahl method, all of which are well known methods to one of ordinary skill in the analytical chemistry art.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed. The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

As previously mentioned, persons who exhibit sensitivity to whole or intact proteins can benefit from consumption of nutritional formulas containing hydrolyzed proteins. Such sensitive persons may especially benefit from the consumption of a hypoallergenic formula.

In some embodiments, the nutritional composition of the present disclosure is substantially free of intact proteins, other than the added lactoferrin. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

Another alternative for pediatric subjects, such as infants, that have food allergy and/or milk protein allergies is a protein-free nutritional composition based on amino acids. Amino acids are the basic structural building units of protein. Breaking the proteins down to their basic chemical structure by completely pre-digesting the proteins makes amino acid-based formulas the most hypoallergenic formulas available.

In a particular embodiment, the nutritional composition is protein-free and contains free amino acids as a protein equivalent source (in addition to lactoferrin). In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 Kcal. In an embodiment, 100% of the free amino acids have a molecular weight of less than 500 Daltons. In this embodiment, the nutritional formulation may be hypoallergenic.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein and/or protein equivalent source per 100 Kcal. In other embodiments, the nutritional composition comprises between about 3.5 g and about 4.5 g of protein or protein equivalent per 100 Kcal.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose, rice starch comprises an amylose: amylopectin ratio of about 20:80, and waxy rice starch comprises only about 2% amylose. Further, tapioca starch generally comprises about 15% to about 18% amylose, and wheat starch has an amylose content of around 25%.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Additionally, in some embodiments the nutritional compositions of the present disclosure comprise at least one source of pectin. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counter ions.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

In some embodiments, the nutritional composition comprises at least one additional carbohydrate, that is, a carbohydrate component provided in addition to the aforementioned starch component. Additional carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can vary from between about 5 g and about 25 g/100 Kcal. In some embodiments, the amount of carbohydrate is between about 6 g and about 22 g/100 Kcal. In other embodiments, the amount of carbohydrate is between about 12 g and about 14 g/100 Kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Particular embodiments of the present compositions include lactose as a carbohydrate source. In one particular embodiment, the additional carbohydrate component of the nutritional composition is comprised of 100% lactose. In another embodiment, the additional carbohydrate component comprises between about 0% and 60% lactose. In another embodiment, the additional carbohydrate component comprises between about 15% and 55% lactose. In yet another embodiment, the additional carbohydrate component comprises between about 20% and 30% lactose. In these embodiments, the remaining source of carbohydrates may be any carbohydrate known in the art. In an embodiment, the carbohydrate component comprises about 25% lactose and about 75% corn syrup solids.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids are found in milk, such as bovine and caprine. In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 Kcals to about 45 mg/100 Kcal. In some embodiments sialic acid may be present in an amount from about 5 mg/100 Kcals to about 30 mg/100 Kcals. In still other embodiments, sialic acid may be present in an amount from about 10 mg/100 Kcals to about 25 mg/100 Kcals.

The present nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, Saccharomyces cerevisiae, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan present in the composition is at between about 0.010 and about 0.080 g per 100 g of composition. In other embodiments, the nutritional composition comprises between about 10 and about 30 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg (3-glucan per day. The nutritional composition may be delivered in multiple doses to reach a target amount of β-glucan delivered to the subject throughout the day. In some embodiments, the amount of β-glucan in the nutritional composition is between about 3 mg and about 17 mg per 100 Kcal. In another embodiment the amount of (3-glucan is between about 6 mg and about 17 mg per 100 Kcal.

It has been found that nutritional supplementation of inositol represents a feasible and effective approach to promote oligodendrocyte survival and proliferation in a dose dependent manner, resulting in a consistent increase in the number of oligodendrocyte precursor cells. Nutritional supplementation with inositol provides benefits for enhanced developmental myelination by which it translates into a fundamental benefit for brain development. Given the importance of functional myelination, nutritional supplementation of inositol is beneficial to pediatric subjects by enhancing brain development and health. Moreover, the sweet taste of inositol provides further advantages in terms of palatability to pediatric consumers.

As such, in certain embodiments, inositol is present in the nutritional compositions of the present disclosure at a level of at least about 4 mg/100 Kcal; in other embodiments, inositol should be present at a level of no greater than about 70 mg/100 Kcal. In still other embodiments, the nutritional composition comprises inositol at a level of about 5 mg/100 Kcal to about 65 mg/100 Kcal. In a further embodiment, inositol is present in the nutritional composition at a level of about 7 mg/100 Kcal to about 50 mg/100 Kcal. Moreover, inositol can be present as exogenous inositol or inherent inositol. In embodiments, a major fraction of the inositol (i.e., at least 40%) is exogenous inositol. In certain embodiments, the ratio of exogenous to inherent inositol is at least 50:50; in other embodiments, the ratio of exogenous to inherent inositol is at least 60:40.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone- 7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The disclosed nutritional composition(s) may be provided in any form known in the art, such as a powder, a gel, a suspension, a paste, a solid, a liquid, a liquid concentrate, a reconstitutable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 Kcal. The amount of protein typically can vary from about 1 to about 7 g/100 Kcal. The amount of carbohydrate typically can vary from about 6 to about 22 g/100 Kcal.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The LGG soluble mediator preparation or nutritional composition comprising the LGG soluble mediator preparation may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to achieve sufficient gut barrier function. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. Each nutritional composition comprises a hydrolyzed protein, at least one pre-gelatinized starch, and at least one pectin. In certain embodiments, the nutritional compositions of the feeding regimen may also include a source of long chain polyunsaturated fatty acid, at least one prebiotic, an iron source, a source of β-glucan, vitamins or minerals, lutein, zeaxanthin, or any other ingredient described hereinabove. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLES

Example 1: SBS Model for Gut Barrier Function

Animals

Forty-eight 5-6 weeks old, male Sprague-Dawley (SD) rats, weighing around 150 g-200 g, were obtained from National Rodent Laboratory Animal Center, Shanghai Branch (Shanghai, China). The rats were housed in individual cages and allowed to acclimatize for 3-5 days under a light-dark cycle of 12 h at constant temperature (22±2° C.), ad libitum to water and chow (M01-F, Shanghai Slac Laboratory Animal Co. LTD) before experiments were initiated.

The experimental protocol was in accordance with the guidelines of the Shanghai Experimental Animal Society, China.

Experiment Design

Forty-eight rats were divided randomly into the following 6 experimental groups of 8 rats each: Sham group (rats underwent a bowel transection with re-anastomosis), SBS group (rats underwent massive small bowel resection, plus 1 mL water by gavage daily), SBS+LEG soluble mediator preparation A group (rats underwent a massive small bowel resection, plus supplemented with LGG soluble mediator desalted by column chromatography), SBS+LEG soluble mediator preparation B group (rats underwent a massive small bowel resection, plus supplemented with LGG soluble mediator desalted by ultrafiltration), SBS+BCM group (rats underwent a massive small bowel resection, plus supplemented with unconditioned bacteria culture medium processed equally as LGG soluble mediator preparation B) and SBS+LGG group (rats underwent a massive small bowel resection, plus supplemented with viable LGG).

Soluble mediator preparation A or B was given in water at an equivalent dosage to $5 \times 10^8$ CFU LGG daily by gavage. Live LGG was given to each rat in 1 mL warm water by intragastric gavage every morning from day 2 throughout day 14 at a dosage of 5×108 CFU/d. Bacterial culture medium (BCM) was diluted and gavaged in the same way as the soluble mediator preparations. Both Sham and SBS rats were gavaged with 1 mL water daily. All rats were ad libitum to lab chow and water. Rats were monitored for 15 days and sacrificed on day 15. Body weight of each rat was measured twice a week.

Operative Procedure

Rats were fasted for 12 hours before the experiment but were allowed free access to water. All operative procedures were performed under anesthesia by intraperitoneal injection of pentobarbital sodium (30 mg/mL), which was administered at doses of 33-40 mg/kg body weight. With the sterile techniques, the abdomen was opened using a midline incision. A sham operation was performed by simple transection of the ileum 5 cm proximal to the ileocecal junction and reanastomosis. Resected animals underwent 75%-80% small bowel resection from 5 cm distal to ligament of Treitz to 10 cm proximal to the ileocecal valve. All anastomoses were performed using interrupted sutures of 5-0 vicryl. Before closure of the abdomen, the rats were resuscitated with a 2 mL intraperitoneal injection of warm 0.9% saline. After recovery, rats were free to water overnight, after which a regular diet was reinstated. All the rats were sacrificed on day 15 by intraperitoneal injection of pentobarbital (75 mg/kg).

2.4 Morphological and Adaptation Evaluation.

Mucosa architecture. The pieces of small intestinal specimens were first rinsed in cold normal saline, then immediately fixed in 10% neutral buffered formalin (pH=7.2). After 72 hours of fixation, the tissue was embedded in paraffin wax on the oriented edge, and cut into 5-μm-thick sections for hematoxylin and eosin staining. The villus height and crypt depth were determined in longitudinal sections using an analysis system. Villus height and crypt depth were measured in 10 vertically well orientated villi and crypts within each sample. The villus height was determined from the crypt opening to the top of the villus, and the crypt depth from the base of the crypt to its opening, using ocular micrometers.

Epithelial Cell Proliferation and Apoptosis.

Terminal deoxynucleotidyl transferase mediated biotinylated dUTP nick end labeling (TUNEL) staining was performed to analyze the apoptosis of intestinal epithelial cells using the In Situ Cell Death Detection Kit (Roche Applied Science, Mannheim, Germany). Apoptosis was expressed as the number of epithelial cells positive to the apoptotic marker per villus. Intestinal epithelial cell proliferation was assessed by immune-histochemical staining for proliferating cell nuclear antigen (PCNA). The index of proliferation was expressed as the number of proliferating cell nuclear antigen-positive cells per crypt in each slide. Serum GLP-2 levels were measured by an enzyme immunoassay kit (Millipore, USA).

Systemic and Local Inflammation 1 ml blood from inferior vena cava was centrifuged at 3000 rpm for 10 min. Serum level of endotoxin was detected using limulus amebocyte lysate (LAL) test (Chinese horseshoe crab reagent Corp, Xiamen, China), expressed as EU/ml. Serum levels of TNF-alpha and IL-6 were detected using ELISA kits (R&D and Antibodies online), expressed as pg/ml. After the luminal contents were removed from the ileum, 100 mg ileum sample was first homogenized in 1 mL PBS, and then centrifuged at 2,000 rpm for 20 min. The supernatant was further collected for cytokine test using ELISA kits.

Intestinal Bacteria Translocation

After the animals were killed, mesenteric lymph nodes (MLN), liver and spleen samples were homogenized and then centrifuged at 1,000 rpm for 10 min. The supernatant was further collected followed by genomic extraction using QIAmp DNA kit. *E. coli* was detected using PCR, using sequence specific primers for *E. coli* beta-galactosidase flank regions.

```
(Primers:
F:
F5'-CTTTGCCTGGTTTCCGGCACCAGA A-3';

R
F5'-AACCACCGCACGATAGAGATTCGGG-3').
```

Intestinal Barrier Function

Intestinal permeability: Fluorescein isothiocyanate-dextran-40,000 Daltons (FD-40) (Sigma-Aldrich, USA) was used to assess intestinal permeability. On day 15, rats were gavaged with 1 mL water containing 5 mg FD-40. At 6 h post-gavage, 1 ml of blood was collected from superior mesenteric vein and centrifuged at 1,000 rpm for 3 min. Plasma samples were diluted in equal volumes of PBS and loaded in duplicate into a 96 well plate. FD-40 concentrations were measured with a fluorescence spectrophotometer (excitation of 490 nm and emission of 520 nm). sIgA level of intestinal content Intestinal contents were collected from proximal ileum within 10 cm to the terminal ileum. 0.2 g sample was weighed and vortexed in 1 mL PBS and centrifuged at 2,000 rpm for 20 min at 4° C. Then, the supernatant was collected and determined by ELISA according to the kit protocol (Alpco, USA).

Tight Junction Expression

The distal ileum of each animal was collected, flushed with ice cold saline solution, and opened along the mesenteric border. The expression of four key tight junction proteins known to regulate intestinal barrier function was examined using Western blotting. Protein band intensity of occludin, ZO-1, claudin-1 and claudin-4 was quantified using Image J software and the relative expressions normalized to actin was used.

Statistical Analysis

Data are reported as mean±SD. The main effects of different nutrients were evaluated by one-way ANOVA or Mann-Whitney U test. Differences between groups were determined by using Fisher's protected least significant difference (LSD) test. Mann-Whitney U test were applied to non-parametric data. The statistical software SPSS for Windows version 17.0 (SPSS Inc., Chicago, Ill., USA) was used for analysis, and a $p<0.05$ was defined as statistically significant.

Weight Changes

All rats had similar body weight from the beginning of this study. Lower body weight was found in all five SBS rats at the time point of 7 and 14 days after bowel resection, compared with the sham group. Within the five SBS groups, all the intervention groups reversed the body weight loss compared with SBS group at the time point of day 14. The body weight of SBS-soluble mediator preparation B and SBS-BCM animals was significantly higher than other SBS rats. Moreover, the treatment groups demonstrated significantly lower weight loss compared to the SBS control group.

TABLE 1

Weight changes among the 6 groups

| | Sham | SBS | SBS-soluble mediator preparation A | SBS-soluble mediator preparation B | SBS-BCM | SBS-LGG |
|---|---|---|---|---|---|---|
| Day 0 | 173.1 ± 1.5 | 176.3 ± 3.3 | 176.5 ± 4.0 | 173.5 ± 5.2 | 171.9 ± 5.8 | 173.3 ± 5.9 |
| Day 7 | 212.5 ± 3.2 | 166.6 ± 3.7$^a$ | 171.2 ± 6.3 | 172.7 ± 6.3$^b$ | 174.6 ± 6.0$^b$ | 169.2 ± 5.0 |
| Day 14 | 254.8 ± 2.5 | 190.0 ± 2.2$^a$ | 198.5 ± 7.3$^b$ | 206.0 ± 6.3$^b$ | 209.6 ± 5.3$^b$ | 197.8 ± 6.4$^b$ |

$^a$P < 0.05 compared with sham group.
$^b$P < 0.05 compared with SBS group

Morphological and Adaptation Evaluation.

Villus height and crypt depth of ileum: Compared with sham rats, all the SBS animals had greater villus height and crypt depth as an adaptive response after small bowel resection. The intestinal morphology is shown in FIG. 1.

TABLE 2

Ileum histology of the six groups

| | Sham | SBS | SBS-soluble mediator preparation A | SBS-soluble mediator preparation B | SBS-BCM | SBS-LGG |
|---|---|---|---|---|---|---|
| Villus height (μm) | 270.6 ± 12.48 | 326.5 ± 24.68$^a$ | 450.9 ± 74.93$^a$ | 421.6 ± 95.70$^a$ | 377.8 ± 27.69$^a$ | 332.4 ± 10.45$^a$ |
| Crypt depth (μm) | 93.7 ± 14.84 | 117.1 ± 15.08$^a$ | 117.0 ± 8.75$^a$ | 114.3 ± 15.64$^a$ | 116.8 ± 12.12$^a$ | 117.1 ± 15.08$^a$ |

$^a$P < 0.05, compared with sham group.

Epithelial Cell Proliferation and Apoptosis.

No difference was detected in apoptotic cell count among the groups. As to proliferation, as marked by PCNA positive cell count per crypt, all the SBS groups tend to have a higher value compared with sham group, but a significant difference was only detected between Sham and SBS-soluble mediator preparation B groups.

TABLE 3

Ileum histology of the six groups

| | Sham | SBS | SBS-soluble mediator preparation A | SBS-soluble mediator preparation B | SBS-BCM | SBS-LGG |
|---|---|---|---|---|---|---|
| Apoptic cell/villus | 7.3 ± 4.6 | 8.3 ± 6.2 | 7.0 ± 5.6 | 8.4 ± 6.0 | 6.6 ± 5.3 | 7.3 ± 5.8 |
| PCNA positive cell/crypt | 3.4 ± 1.7 | 5.4 ± 1.8 | 5.0 ± 1.7 | 5.2 ± 1.2 | 4.9 ± 1.8 | 5.1 ± 2.8 |

$P < 0.05$, comparison between groups with different letter in the upper right corner.

Intestinal Growth Factor-GLP2 Levels.

Among all the massive intestinal resection groups, SBS-soluble mediator preparation B and SBS-BCM rats showed increased GLP-2 levels than the SBS group ($P<0.05$). See FIG. 3A.

Systemic and Local Inflammation

Serum Endotoxin

Serum endotoxin levels were significantly increased in all the massive intestinal resection groups compared with sham group ($P<0.05$). All the intervention groups showed lower endotoxin levels compared with SBS group ($P<0.05$). See FIG. 3B.

Cytokine levels: The cytokine levels in the six treatment groups are summarized in table 4. Inflammatory cytokines were significantly increased in all the massive intestinal resection groups compared with sham group ($P<0.05$). LGG soluble mediator preparations A and B significantly decreased cytokine levels.

TABLE 4 cytokine levels of 6 groups

| | Sham | SBS | SBS-soluble mediator preparation A | SBS-soluble mediator preparation B | SBS-BCM | SBS-LGG |
|---|---|---|---|---|---|---|
| Serum TNF-α | 35.2 ± 4.11 | 74.6 ± 5.43[a] | 55.3 ± 3.49[b] | 55.5 ± 2.96[b] | 49.2 ± 2.57[b] | 55.7 ± 2.37[b] |
| Ileum TNF-α | 76.1 ± 27.23 | 490.2 ± 24.54[a] | 397.6 ± 44.41[b] | 356.0 ± 30.56[b] | 267.6 ± 23.0[b] | 385.8 ± 54.82[b] |
| Serum IL-6 | 124.3 ± 24.40 | 215.4 ± 31.09[a] | 171.4 ± 14.05[b] | 159.4 ± 26.70[b] | 146.4 ± 25.36[b] | 188.8 ± 38.76 |
| Ileum IL-6 | 148.8 ± 12.91 | 540.3 ± 35.21[a] | 467.2 ± 88.75 | 506.4 ± 23.07 | 360.7 ± 40.81[b] | 410.7 ± 70.74[b] |

[a]$P < 0.05$, compared with sham group
[b]$P < 0.05$ with SBS group

Intestinal Bacteria Translocation

Each intervention group showed significantly less enteral bacterial translocation to nearby organs compared with SBS group, as summarized in Table 5.

TABLE 5

Relative expression ($2^{-\Delta\Delta Ct}$) of E. coli. of different organs in the six groups

| | Sham | SBS | SBS-soluble mediator preparation A | SBS-soluble mediator preparation B | SBS-BCM | SBS-LGG |
|---|---|---|---|---|---|---|
| MLN | 1.03 ± 0.27 | 13.05 ± 5.38[a] | 6.78 ± 2.34[b] | 6.00 ± 1.44[b] | 5.77 ± 0.72[b] | 6.24 ± 1.92[b] |
| Liver | 1.05 ± 0.38 | 3.75 ± 0.74[a] | 2.80 ± 0.78[b] | 2.78 ± 0.55[b] | 2.42 ± 0.57[b] | 2.77 ± 0.75[b] |
| Spleen | 1.05 ± 0.36 | 2.22 ± 0.18[a] | 1.39 ± 0.14[b] | 1.63 ± 0.32[b] | 1.48 ± 0.2[b] | 1.65 ± 0.27[b] |

[a]$P < 0.05$, compared with sham group
[b]$P < 0.05$ with SBS group

Intestinal Barrier Function

Intestinal permeability: Serum FD-40 (Fluorescein isothiocyanate-dextran-40,000 Daltons) levels were significantly increased in all the massive intestinal resection groups compared with sham group (P<0.05). All the intervention groups showed improved intestinal permeability compared with SBS group. See FIG. 3C.

Intestinal barrier resistance functions: sIgA of intestinal content: The sIgA level was significantly increased in all the intervention groups compared with SBS group (P<0.05). SBS-soluble mediator preparation B showed higher sIgA levels than the SBS-LGG group (P<0.05). See FIG. 3D.

Summary of Results

As compared to the SBS group, enteral supplementation of LGG soluble mediator preparations after massive bowel resection helps to reduce bacterial translocation, improve intestinal adaptive responses, intestinal barrier resistance and intestinal barrier function as well.

When compared to the SBS group, both SBS-soluble mediator preparation A and SBS-soluble mediator preparation B showed better weight gain, adaptation, lower inflammatory cytokine levels and intestinal permeability, and less intestinal bacteria translocation as well. Both groups showed similar improvement in most indices, soluble mediator preparation B showed better maintenance of tight junction protein levels compared with soluble mediator preparation A. Both LGG soluble mediator preparations showed better results than LGG in some of the indices.

Example 2: Visceral Pain Study

Animals

Male and female Sprague-Dawley rats were purchased from Harlan UK. These rats were mated in the Preclinical Research Facility, Bioscience Institute, University College Cork and the subsequent offspring were used in the following experiments. The resulting dams and litters were housed in large breeding cages in a temperature- and humidity-controlled room on a 12 h light, 12 h dark cycle (lights on 0700-1900 h). All experiments were conducted in accordance with the European Directive 2010/63/EEC, the requirements of the S.I No 543 of 2012, and approved by the Animal Experimentation Ethics Committee of University College Cork.

Experimental Design

Maternal separation protocol was started at birth (PND0), litters were randomly assigned to undergo maternal separation or remain as non-separated controls.

PND0: the pups were counted with as little disturbance to mothers and pups as possible. Handling was kept minimum at this time.

PND2: the litters assigned to MS were removed from the main colony room to an adjacent room. Mothers were first removed from the home cage and placed into a smaller holding cage. Following this, the entire pups from the same litter were gently placed into a small cage. Mothers were returned to the home cage and the main colony room without their ups. The cage containing the pups remained in the adjacent room to allow no sound from the mother was passed to the pups and vice versa. All rooms were maintained at the same temperature (21°±2° C.) and lighting conditions as the main colony room, and placed on a heating pad set at 30-33° C. for 3 h. After the 3 h separation, the mothers were again brought into the adjacent room and placed briefly in a holding cage while pups were returned to the original home cage. This was followed immediately by the return of the mother.

Non-separated litters were left undisturbed in the mothers' home cage except for routine cage cleaning performed once a week. This maternal separation procedure was performed from PND2 to PND12 (inclusive). The period of separation was carried out at the same time daily.

PND21 weaning: male and female offspring were grouped based on sex. Both MS and non-separated NS male rats were used for the supplementation experiments. This was done in 2 successive cohorts. For each cohort, 48 rates were randomly group-housed by treatment, 2 cages per treatment, and 3 rats per cage, with no littermates housed together. Supplementation groups are described in Table 1. Diet and water supplementations began as soon as pups were weaned from the dam on PND21. Two LGG soluble mediator preparations (A and B) or unconditioned bacterial culture medium (BCM) as a reference were supplemented to the drinking water. Soluble mediator preparations were supplemented to drinking water to give a dose equivalent to a range from $1.3 \times 10^8$ to $4.3 \times 10^8$ viable LGG/animal/day throughout the study until PND 85. Visceral hypersensitivity was assessed at PND 79. Body weight was measured weekly, water intake daily, and feed intake 3 times/week.

Visceral Sensitivity Assessment

Assessment was performed by colorectal distension. Animals were fasted for 24 h and then lightly anesthetized. A 6 cm polyethylene balloon with a connecting catheter was inserted in the distal colon 1 cm proximal to the anus. The catheter was fixed to the tail with tape to avoid displacement. Animals were allowed to recover from anesthesia for at least 15 minutes before commencing colorectal distension.

A customized barostat was used to control air inflation and pressure during colorectal distension. The distension paradigm used was an ascending phasic distension from 0 to 80 mmHg. A trained observer scored each rat for the threshold, or pressure when the first pain behavior is noted. A summary of the treatment groups is provided in Table 6 below:

TABLE 6

Treatment Groups

| Group | Drink supplementation | Condition | Number (total) |
| --- | --- | --- | --- |
| 1 | None | Non-separated (NS) | 12 |
| 2 | None | Maternally-separated (MS) | 12 |
| 3 | Soluble mediator prep A | NS | 12 |
| 4 | Soluble mediator prep A | MS | 12 |
| 5 | Soluble mediator prep B | NS | 12 |
| 6 | Soluble mediator prep B | MS | 12 |
| 7 | BCM | NS | 12 |
| 8 | BCM | MS | 12 |

Growth and Intakes

Figure 4A:
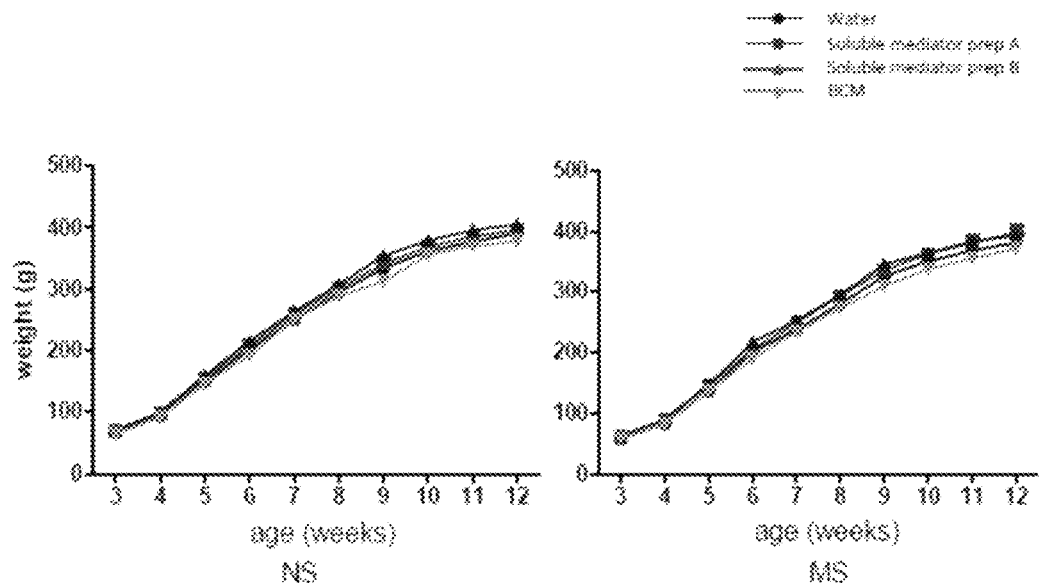
FIGS. 4A-C are graphs demonstrating that drinking water supplementations and early life stress did not affect (4A) weight gain; (4B) food intake; or (4C) liquid intake. (NS— Non separated; MS—maternally separated).
Figure 4B:
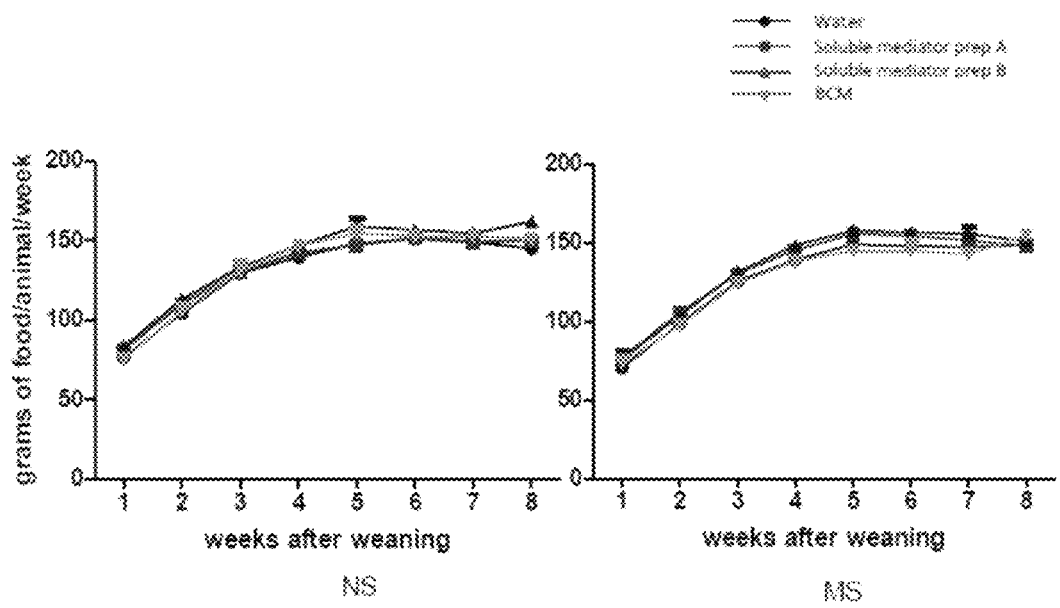
Figure 4C:
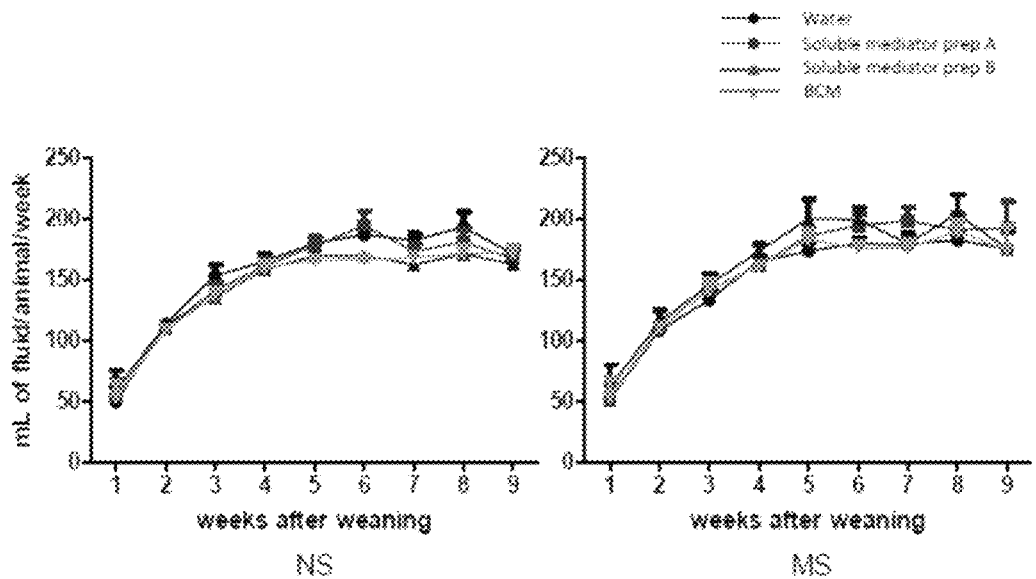

All rats showed no differences in initial or terminal body. Early life condition (NS or MS) or drinking supplementation had no effect on weight gain, food intake or fluid intake (FIGS. 4A-4C).

Visceral Pain

Figure 5:
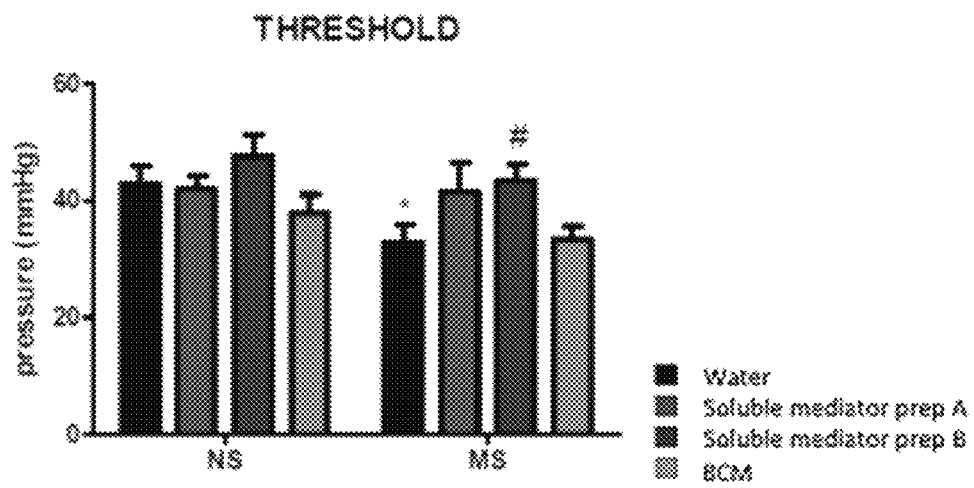
FIG. 5 is a graph showing that a soluble mediator preparation (soluble mediator preparation B) ameliorates visceral pain hypersensitivity induced by early life stress. Values are mean±sd, (*)p=34 vs. NS-water; (#)p=0.03 vs. MS-water.

Early life stress induced by maternal separation lowered threshold of pain perception in rats when compared to the NS animals (p=0.034) during colorectal distension performed at adult life. This is ameliorated by soluble mediator preparation B, showing increased pain threshold to colorectal distension when compared to MS-rats drinking water without any supplementations (p=0.03) (FIG. 5).

Example 3: Preparation of LGG Soluble Mediator Preparations

During a first LGG batch fermentation (200 L), samples of 10 L were collected at 3 time points (mid exponential, late exponential and stationary phase) for determination of OD600 and CFU and further processing. Biomass was removed from the suspension by centrifugation. Supernatant from these 3 sampling points were collected and frozen at −20° C., labelled MEG, LEG, SEG, respectively. Based on a bioactivity assay, spent culture medium collected at late exponential growth (LEG) exhibited the highest cytokine induction. Late exponential growth sampling corresponds to approx. 15 hour fermentation time. Fermentation is also monitored by corresponding OD values and base uptake to maintain the pH during fermentation).

The culture medium described in Table 7 results in a high amount of biomass.

TABLE 7

Bacterial culture medium composition.

| Component | Composition MRS medium for LGG bottles (g) | Adapted MRS medium for LGG 200 L fermenter (kg) |
|---|---|---|
| Solution 1 | | |
| Glucose, $H_2O$ | 66 | 13.2 |
| Demineralized Water | 84 | 10.8 |
| Solution 2 | | |
| Tween ® 8- | 2. | 0.4 |
| Na-acetate 3 $H_2O$ | 10.0 | 2.0 |
| $NH_4Cl$ | 2.6 | 0.528 |
| $Na_3$ citrate 2 $H_2O$ | 4.8 | 0.960 |
| $K_2H_3PO_4$ | 4.0 | 0.800 |
| $MgSO_4$ $7H_2O$ | 0.4 | 0.080 |
| $MnSO_4$ $H_2O$ | 0.008 | 0.016 |
| Yeast Extract (Gistex LS, powder | 46 | 9.2 |
| Demineralized water | 780 | 162 |

The presence of Tween 80 is not considered desirable or even acceptable for use in nutritional products for relatively vulnerable subjects, such as infant formula. Therefore, it was determined if Tween 80 could either be left out or be replaced by more natural oils or fatty acids as surfactant. Growth of LGG in medium without Tween 80 was comparable to growth on medium with Tween. None of the replacement oils induced better growth. Therefore, it was concluded that Tween 80 could be removed from the culture medium and media for all further fermentations did not contain Tween 80 anymore.

A second 200 L batch fermentation was performed in a similar way without addition of Tween 80 (2). About 30 L spent medium samples were collected at late exponential growth phase after removal of biomass. Spent medium was desalted, sterile filtrated (0.2 µm), and lyophilized. By desalting, lactic acid produced during the fermentation is removed; this step has been included to be able to assess effects of bacterial metabolites other than lactic acid and to avoid difficulties during drying of the material. Microfiltration (=sterile filtration) ensures the absence of any intact bacterial cells. Lyophilization (=freeze drying) is an option to obtain dried material from a liquid.

Selection of Desalting Buffer and Method

The desalting process was performed by 2 different methods: Column Chromatography (CG) or Ultrafiltration (UF). Initially, sodium acetate buffer was used for both processes (2). Low molecular molecules (<6 kDa for CG, <5 kDa for UF), including lactic acid, were removed by desalting. The >6 kDa and >5 kDa fractions, respectively, were collected for further evaluations. Desalted liquid coming out of the CG column (>6 kDa) was labelled soluble mediator preparation A. Retentate from UF (>5 kDa) was labelled soluble mediator preparation B.

It was determined, however, that residual sodium acetate in the final product is not desirable. This includes residual sodium acetate that comes from cultivation media or processing aids, such as buffer used for the desalting process. To avoid the presence of sodium acetate from the final preparations, an alternative buffer for the desalting process, namely potassium citrate, was recommended. Culture supernatant obtained from the two different desalting protocols using the two different buffers were tested in the standard in vitro assay to gain preliminary insights in the effect of process changes on bioactivity. The results showed comparable cytokine production by preparations obtained from CG (soluble mediator preparation A) and UF (soluble mediator preparation B). From a technological perspective, soluble mediator preparation B is preferable over soluble mediator preparation A for upscaled production since column chromatography is very difficult to apply on large amounts of material. However, to gain a better understanding on bioactivity, currently as far as possible both soluble mediator preparations are included in the preclinical bioactivity assessments. The desalted culture supernatant prepared on lab scale was dried by lyophilization (freeze-drying) prior to being used in the non-clinical assays.

Although preferred embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. A method for i) promoting gut barrier regeneration, ii) promoting gut barrier maturation and/or adaptation, iii) supporting gut barrier resistance and/or iv) protecting gut barrier function in a pediatric subject in need thereof, comprising:

administering to the pediatric subject a composition comprising an effective amount of a soluble mediator preparation from a late-exponential growth phase of a *Lactobacillus rhamnosus* GG (LGG) batch-cultivation process, wherein the soluble mediator preparation is produced by (a) subjecting LGG to cultivation in a suitable medium using a batch process; (b) harvesting a culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5 or 6 kDa; (d) removing any remaining cells by 0.2 μm sterile filtration to provide the soluble mediator preparation; (e) removing liquid contents from the soluble mediator preparation so as to obtain the composition.

2. The method of claim 1, wherein the pediatric subject has impaired gut barrier function or loss of gut integrity.

3. The method of claim 1, wherein the pediatric subject has short bowel syndrome or necrotizing enterocolitis.

4. The method of claim 1, wherein the pediatric subject is an infant.

5. The method of claim 4, wherein the pediatric subject is a preterm infant.

6. The method of claim 1, wherein step (b) further comprises removal of bacterial cells by sterile filtration.

7. The method of claim 1, wherein the late exponential phase is defined with reference to the latter quarter portion of the time between the lag phase and the stationary phase of the batch-cultivation process.

8. The method of claim 1, wherein the batch cultivation is conducted in a culture medium devoid of polysorbates.

9. The method of claim 7, wherein the medium contains an ingredient selected from the group consisting of oleic acid, linseed oil, olive oil, rape seed oil, sunflower oil, and mixtures thereof.

10. The method of claim 1, wherein the batch cultivation is conducted at a pH of from 5-7.

11. The method of claim 1, wherein the composition is a pediatric nutritional composition.

12. The method of claim 1, wherein the effective amount is equivalent to about $1 \times 10^4$ to about $1 \times 10^{12}$ cell equivalents of live probiotic bacteria per kg body weight per day.

13. The method of claim 1, the composition further comprising arachidonic acid and docosachexaenoic acid, wherein the ARA and DHA are present in a weight ratio ranging from about 1:3 to 9:1.

14. The method of claim 1, wherein the composition is an infant formula.

15. The method of claim 1, wherein the composition further comprises lactoferrin.

16. The method of claim 15, wherein lactoferrin is present in an amount of from about 10 mg/100 Kcal to about 200 mg/100 Kcal.

17. The method of claim 1, wherein the composition further comprises prebiotics.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

```
Arg Arg Arg Arg
1

<210> SEQ ID NO 2
<211> LENGTH: 4
<212> TYPE: PRT
<213> ORGANISM: Homo sapiens

<400> SEQUENCE: 2

Arg Lys Val Arg
1

<210> SEQ ID NO 3
<211> LENGTH: 26
<212> TYPE: PRT
<213> ORGANISM: Bos taurus

<400> SEQUENCE: 3

Phe Lys Cys Arg Arg Trp Gln Trp Arg Met Lys Lys Leu Gly Ala Pro
1               5                   10                  15

Ser Ile Thr Cys Val Arg Arg Ala Phe Ala
            20                  25
```